US00PP17698P3

(12) United States Plant Patent
Michalik

(10) Patent No.: US PP17,698 P3
(45) Date of Patent: May 8, 2007

(54) **VARIETY OF *GERANIUM* PLANT NAMED 'PENLAVA'**

(50) Latin Name: *Pelargonium×hortorum*
Varietal Denomination: Penlava

(75) Inventor: Andrea Michalik, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 1145 days.

(21) Appl. No.: 09/739,023

(22) Filed: Dec. 8, 2000

(65) Prior Publication Data

US 2003/0213040 P1 Nov. 13, 2003

(51) Int. Cl.
*A01H 5/00* (2006.01)

(52) U.S. Cl. ..... Plt./329
(58) Field of Classification Search ..... Plt./329
See application file for complete search history.

(56) References Cited

U.S. PATENT DOCUMENTS

| | | | | | |
|---|---|---|---|---|---|
| PP7,087 | P | * | 12/1989 | Hofmann | Plt./329 |
| PP9,216 | P | * | 7/1995 | Klemm | Plt./329 |
| PP10,018 | P | * | 9/1997 | Lemon | Plt./329 |
| PP12,411 | P2 | * | 2/2002 | Hanes | Plt./329 |

OTHER PUBLICATIONS

UPOV ROM GTITM Computer Database GTI Jouve Retrieval Software 2003/04 Citations) for 'Penlava'.*

* cited by examiner

*Primary Examiner*—Kent Bell
*Assistant Examiner*—W. C. Haas
(74) *Attorney, Agent, or Firm*—The Webb Law Firm

(57) ABSTRACT

A new and distinct zonal *geranium* plant with intense purple colored flowers above medium green foliage. The plant flower is suitable for pot planting and as a bedding plant.

2 Drawing Sheets

Botanical classification: *Pelargonium×hortorum.*
Varietal denomination: 'Penlava'.

BACKGROUND OF THE INVENTION

The present invention comprises a new and distinct cultivar of *Pelargonium×hortorum* known by the varietal name 'Penlava'. The new variety was discovered in 1994 in a selective breeding program in Dresden, Germany. The new variety is the result of the crossing of dark leafed breeding varieties. The exact parents are unknown. The new variety was first asexually reproduced by cuttings in Dresden, Germany in 1995. The new variety has been trial and field tested and has been found to retain its distinctive characteristics and remain true to type through successive propagations.

DESCRIPTION OF THE DRAWING

The accompanying photographic drawings illustrate the new variety, with the color being as nearly true as is possible with color illustrations of this type.

DESCRIPTION OF THE PLANT

Figure 1:
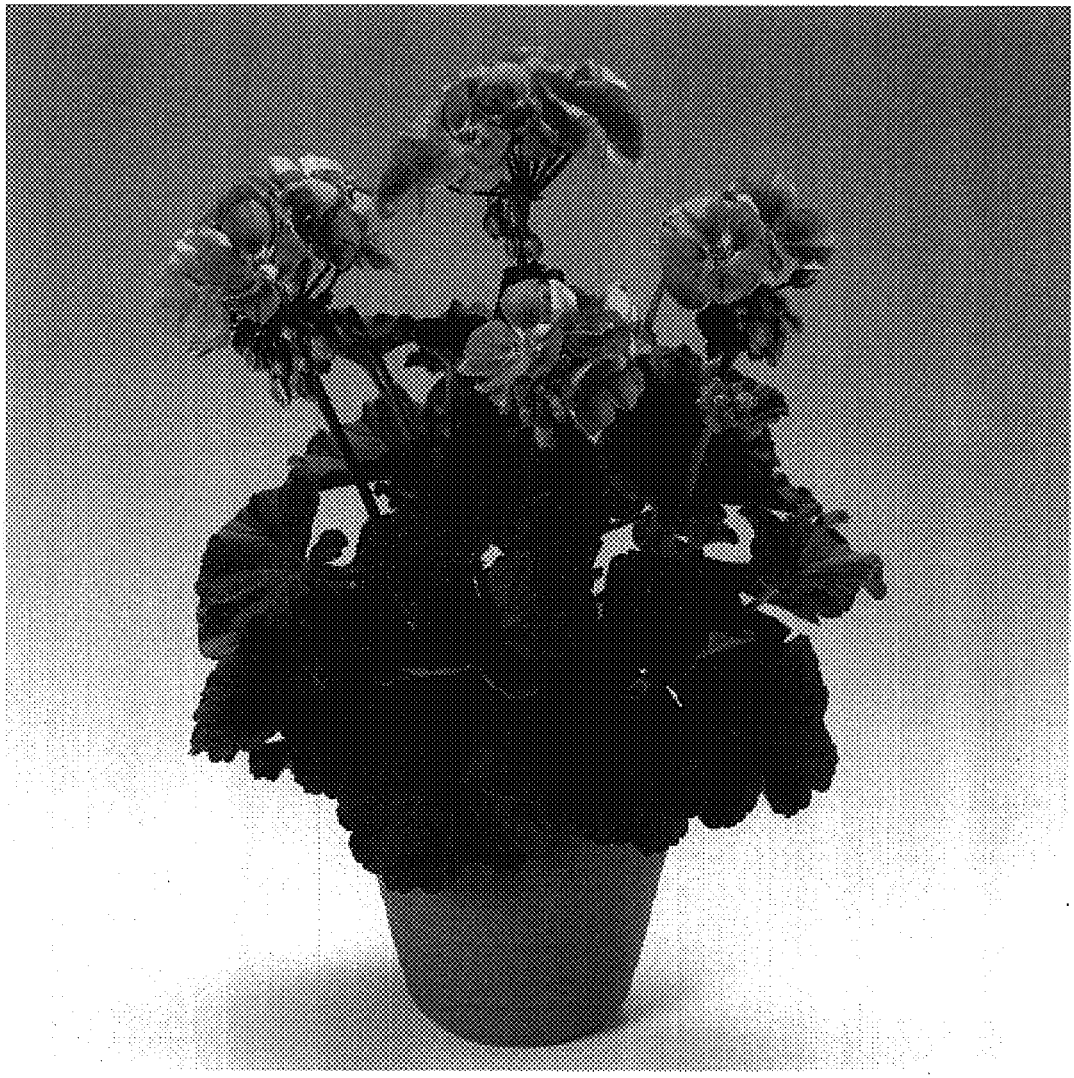
FIG. 1 is a photograph of the entire plant.
Figure 2:
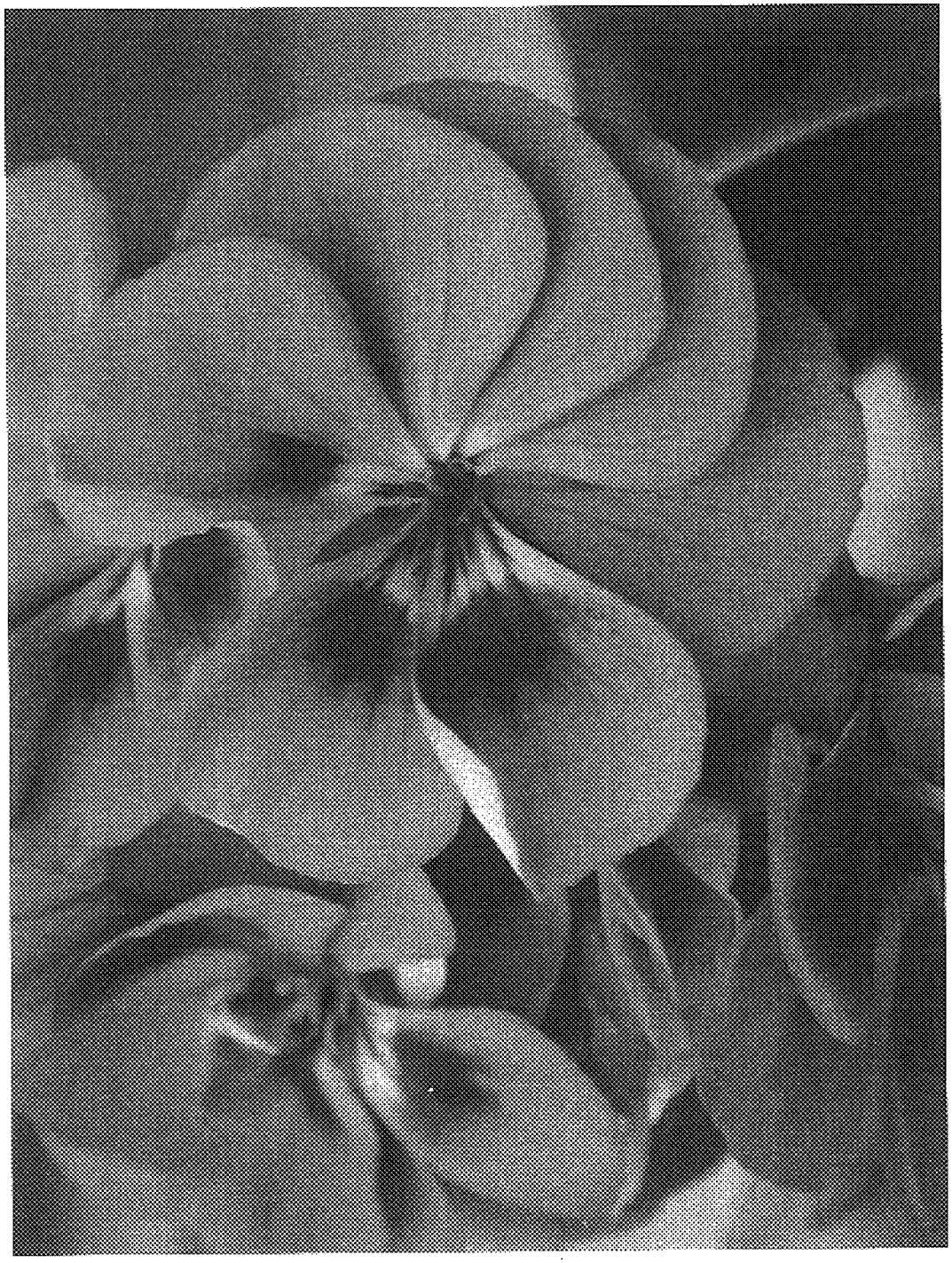
FIG. 2 is a close-up of the flowers of the new variety.

The following detailed description sets forth the characteristics of the new cultivar. The data which defines these characteristics were collected by asexual reproductions carried out in Dresden, Germany. Plants were grown in greenhouse conditions and were nine months old when described. The color readings were taken outdoors in shadow during summer. Color references are primarily to The R.H.S. Colour Chart of The Royal Horticultural Society of London.

PLANT

Classification:
*Botanical.*—*Pelargonium×hortorum.*
*Commercial.*—Zonal *geranium.*
Form: Erect.
Height from media surface to top of foliage: 40 cm.
Height from media surface to top of umbel: 50 cm.
Average spread: 30 cm.
Growth: Medium degree of branching.
Strength: Does not require artificial support.
Response time:
*Time from cutting until plant is rooted.*—3.5 weeks.
*Time from cutting until plant flowers.*—3.5 months.
Leaves:
*Size.*—8–10 cm long; 8 cm wide.
*Shape.*—Cordate.
*Margin.*—Partially toothed.
*Texture.*—Hairy.
*Color.*—Green Group 139A with weak zone of 147A.
*Ribs and veins.*—Color: Brighter than leaf surface.
Petioles:
*Color.*—147B.
*Length.*—6–8 cm.
*Diameter.*—3 mm.
*Strength.*—High.
*Surface texture.*—Rough.
Stem/branches:
*Length.*—20–25 cm.
*Width.*—10 mm.
*Color.*—139A.
*Internode length.*—4–6 cm.

THE BUD

Shape when just showing color:
*Overall.*—Spherical.
*Individual bud.*—Elliptical.
Color: Green Group 136B.
Size when just showing color:
*Umbel.*—8–10 cm across.
*Individual bud.*—1.2 cm long; 0.6–0.8 cm wide.

INFLORESCENCE

Average number of flowers per inflorescence: 10–15.
Blooming habit: Semi-double.
Size of fully open bloom: 4.5 cm across.
Borne: Flowers on umbel; umbel on pedicel; pedicel on peduncle.
Flowers:
*Form.*—Zygomorph.
*Number of petals.*—7–9.
*Petals.*—Length: 25 mm. Width: 23 mm. Shape: Fan-shaped. Margin: Entire. Color: Upper surface: Purple Group 78C. Lower surface: Purple Group 75C.
*Eye color.*—57A.
*Texture and appearance.*—Velvety.
Petaloids: Absent.
Pedicel:
*Length.*—2.0–2.5 cm.
*Color.*—Reddish-green.
Peduncle:
*Length.*—10 cm.
*Color.*—Reddish-green.

Disease/pest resistance: No unusual susceptibility to diseases or pests has been noted to date.
Weather tolerance: Very heat tolerant, not cold tolerant.
Lasting quality: Long-lasting; 4 weeks per umbel.

REPRODUCTIVE ORGANS

Stamens:
*Anthers.*—3 mm long.
*Filaments.*—Length: 0.5 cm maximum. Color: White.
*Pollen.*—Orange.
Pistils:
*Number.*—Five.
*Length.*—0.3–0.4 cm.
*Stigma.*—Pink.
*Style.*—0.8 cm long.
*Shape.*—Actinomorphic.
Ovaries:
*Color.*—Greenish.
*Length.*—0.4 cm.
Fruit: Very rarely present.

GENERAL CHARACTERISTICS

1. Dark-leafed.
2. Intense flower color with eye.
3. Shiny flower color.
4. Vigorous growth habit.

I claim:

1. A new and distinct variety of *geranium* plant substantially as shown and described.

* * * * *